United States Patent [19]

Ivory et al.

[11] Patent Number: 5,200,050
[45] Date of Patent: Apr. 6, 1993

[54] ELECTROPHORETIC PROCESSOR AND METHODS

[75] Inventors: Cornelius F. Ivory; William A. Gobie, both of Pullman, Wash.

[73] Assignee: Washington State University Research Foundation, Pullman, Wash.

[21] Appl. No.: 782,692

[22] Filed: Oct. 25, 1991

[51] Int. Cl.⁵ .................... G01N 27/26; G01N 27/447
[52] U.S. Cl. ............................ 204/299 R; 204/180.1; 204/301
[58] Field of Search ................ 204/299 R, 301, 180.1, 204/183.2

[56] References Cited

U.S. PATENT DOCUMENTS 4,900,421  2/1990  Grutzner et al. ............... 204/299 R

OTHER PUBLICATIONS

Rotofor brochure entitled *A Revolutionary Device for High Resolution Preparative Electrophoresis* by Bio-Rad Laboratories Chemical Division (undated).
Article entitled, *The Development of Recycle Zone Electrophoresis* by Cornelius F. Ivory, Department of Chemical Engineering, Washington State University, 1990.

Primary Examiner—John Niebling
Assistant Examiner—John S. Starsiak, Jr.
Attorney, Agent, or Firm—Wells, St. John, Roberts, Gregory & Matkin

[57] ABSTRACT

An electrophoretic processor for separating proteins and other chemicals exhibiting varying electrophoretic mobilities. The preferred processor includes a rotor which turns within a stator to define a processing chamber therebetween. The rotor and stator are preferably cylindrical to provide an cylindrically annular processing chamber which will induce transverse secondary flows, preferably in the form of toroidal vortices. The transverse toroidal vortices improve heat transfer and counteract longitudinal flows which decrease separation. The processor can be provided with a process temperature stabilizer, such as a chamber surrounding the stator, through which a heat exchange fluid is passed. The processor can be used to perform a variety of processes including batch and continuous flow zone electrophoresis and batch isoelectric focusing.

51 Claims, 9 Drawing Sheets

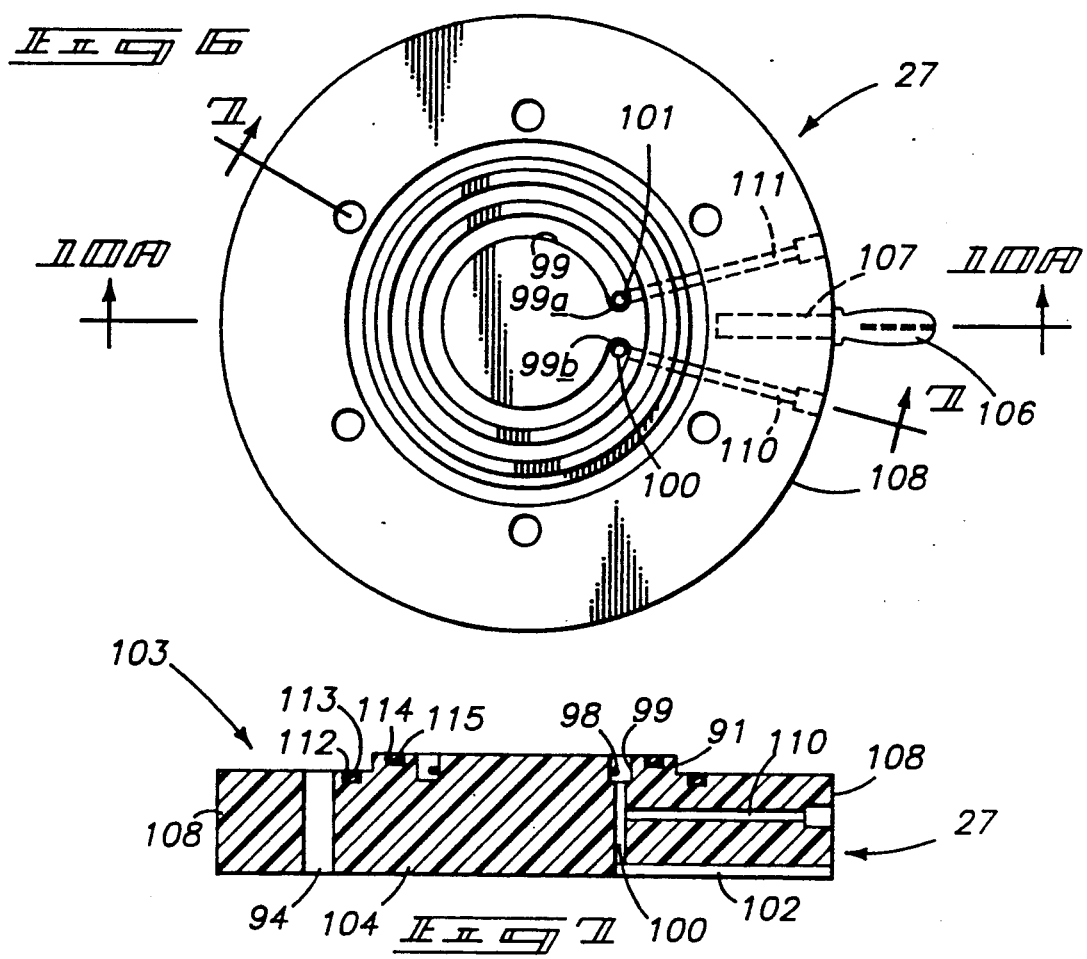
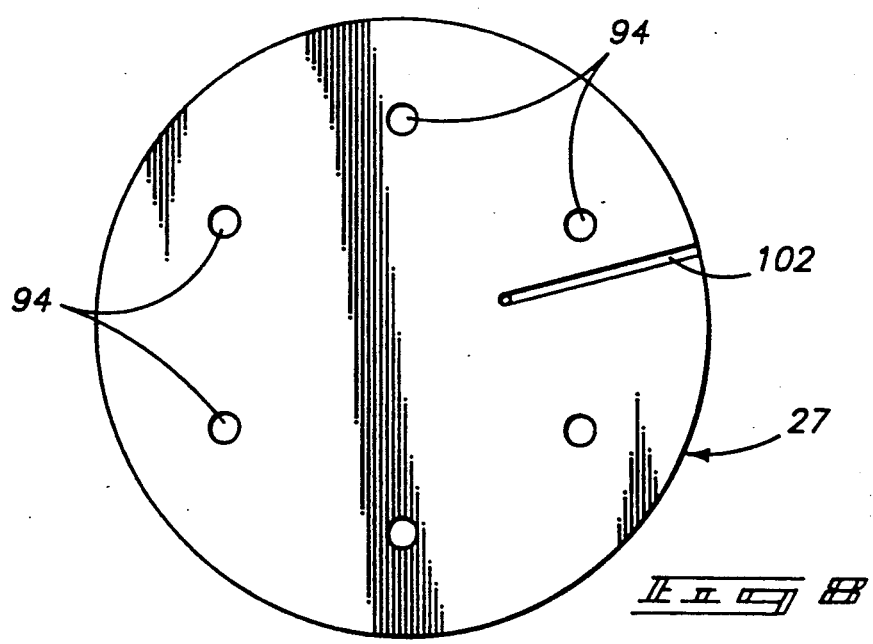

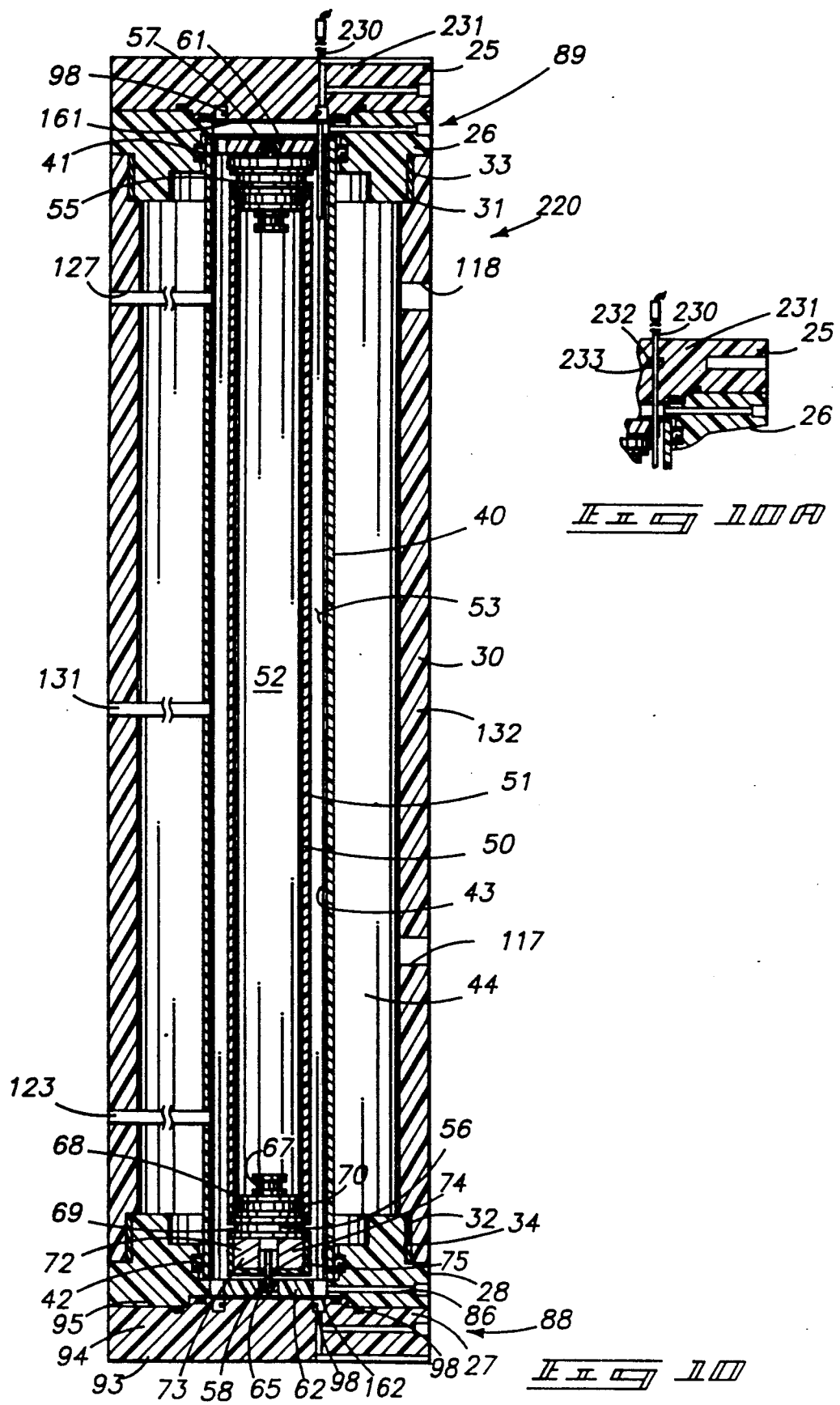

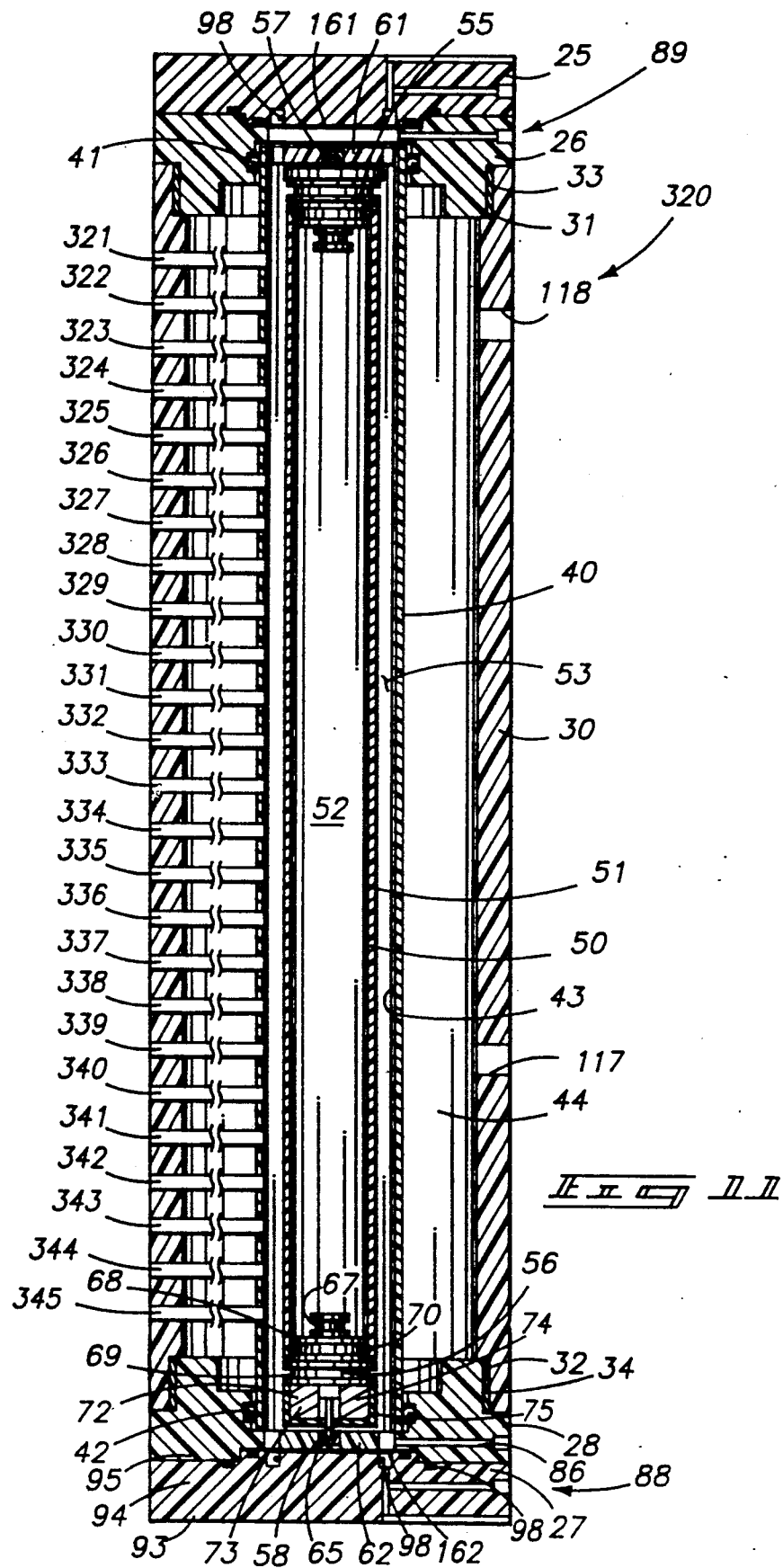

ELECTROPHORETIC PROCESSOR AND METHODS

TECHNICAL FIELD

The technical field of this invention is electrophoretic processors and related methods of electrophoretic processing, particularly electrophoretic separation of proteins.

BACKGROUND OF THE INVENTION

Over the last 20 years there have been great advancements in protein synthesis, recombinant organism expression of complex molecules, particularly proteins, and hybridization of cells to produce monoclonal antibodies. These and other developments have lead to increasing need for apparatus and methods for efficiently separating desired products from co-products and various other contaminants.

Electrophoresis has been previously used for protein and peptide separation. However, electrophoresis has in general been performed at low flow rates not adapted to preparative scale production to provide significant quantities of the desired products. Many prior art electrophoretic separation systems utilize a confined chamber formed between two plates. An electric field is established between two opposing electrodes or in a desired two-dimensional array using additional electrodes. Such systems typically have good resolution of proteins but have limited flow rates. They are also typically limited to a single type of processing. They are further relatively complex and costly and troublesome to operate at preparative scale sizes. Preparative scale systems must be contrasted to laboratory scale systems used to discriminate proteins contained in samples for identification and extraction in very limited quantities.

One preparative scale electrophoresis apparatus is the ROTOPHOR® by Bio-Rad Laboratories of Richmond, Calif. 94804. This apparatus performs preparative scale free solution isoelectric focusing of proteins using a rotating electrophoretic processing chamber. The rotating electrophoretic processing chamber has a horizontal axis of rotation which extends between the electrodes. The processing chamber is divided into twenty (20) discrete compartments using membrane screens which are transversely placed along the horizontal axis. An ampholyte solution is used to create a pH gradient between the charged electrodes. The varying pH along the chamber allows proteins to selectively collect (focus) at the pH corresponding to their associated isoelectric points. Thus proteins having differing isoelectric points can in many cases be separated into one of the discrete compartments.

The ROTOPHOR performs only in a batch mode of operation and only performs isoelectric focusing. The batch operation takes about 4 hours, thereby limiting the processing rates which can be achieved. This unit further must be stopped to extract the separated proteins and cannot be used in a continuous flow mode of operation. The separated fractions are removed using a harvesting apparatus having a series of tubes which tap the processing chamber at various fixed locations along the axis between the electrodes. This unit is also relatively costly to purchase and operate.

The apparatus of the current invention is advantageous in providing a construction having features which allow it to be used for several different types of electrokinetic separation. Electrophoresis can be performed in both batch and continuous flow modes of operation. Additionally, batch isoelectric focusing can be performed and extraction at various locations from the processing chamber can be accomplished. The system is relatively less complex than prior systems. It is also relatively low cost in both operation and initial construction of the system. It further provides improved heat transfer and resists problems due to electroosmosis while providing good separation of most proteins or other processed chemicals of varying electrophoretic mobilities.

BRIEF DESCRIPTION OF THE DRAWINGS

One or more preferred forms of the invention are described herein with reference to the accompanying drawings. The drawings are briefly described below.

FIG. 6 is a top view of the bottom electrode holder forming part of the processor of FIG. 1 in isolation.

FIG. 7 is a sectional view of the bottom electrode holder of FIG. 6 taken along section line 7—7 thereof.

FIG. 8 is a bottom view of the bottom electrode holder shown in FIG. 6.

FIG. 10 is a longitudinal sectional view similar to FIG. 2 showing an alternative embodiment.

FIG. 10A is an enlarged sectional view showing the catheter mounting portion forming a part of FIG. 10.

FIG. 11 is a longitudinal sectional view similar to FIG. 2 showing a further alternative embodiment.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Electrophoretic Processors

Figure 1:
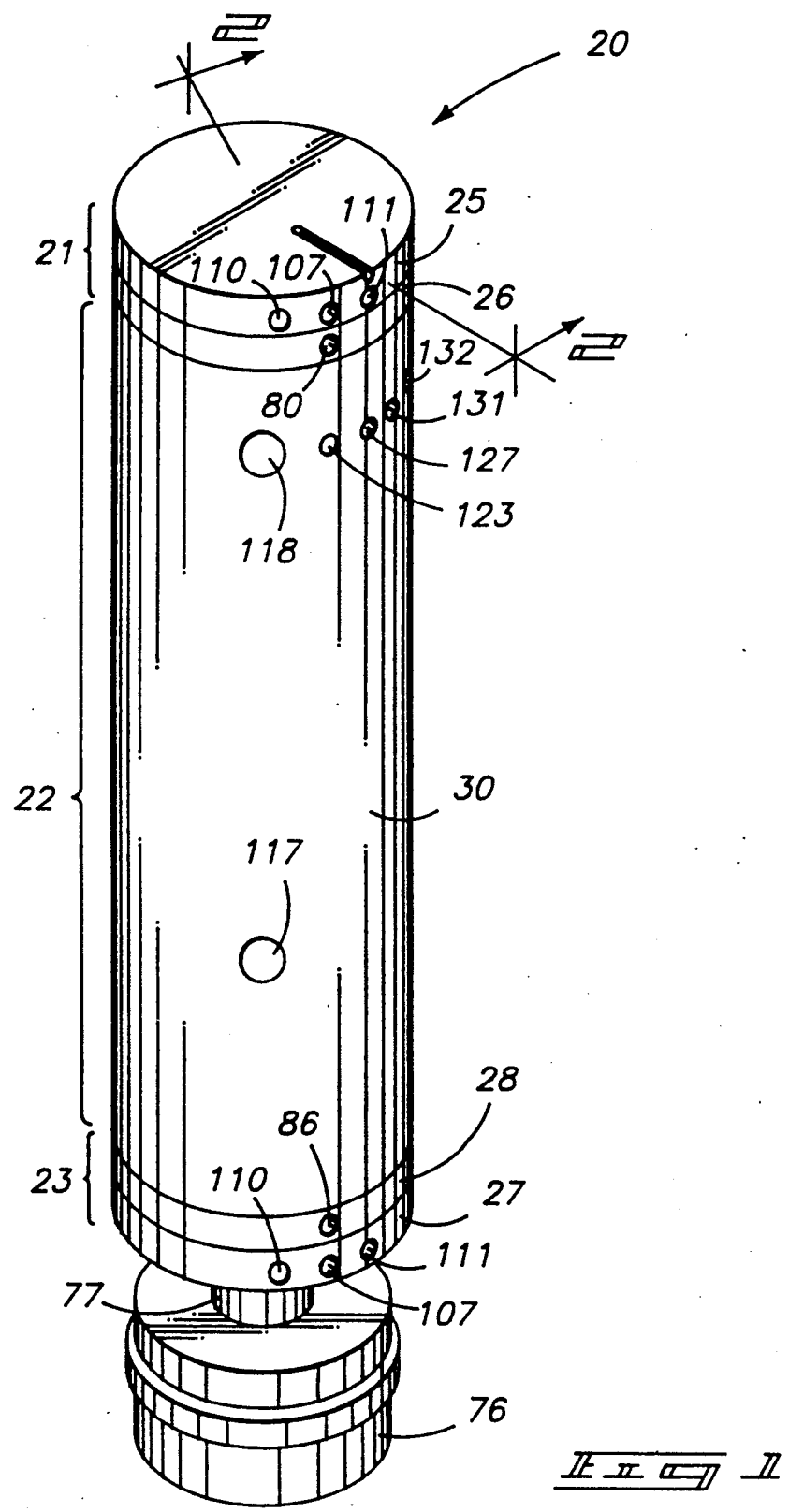
FIG. 1 is a perspective view showing a novel electrophoretic processor constructed according to the principles of this invention.

FIG. 1 shows a preferred electrophoretic processor 20 constructed according to this invention. Processor 20 includes a top end section 21, central section 22 and bottom end section 23. The top or first end section 21 includes a top or first electrode holder 25. It also includes a top or first end piece 26. The bottom or second end section 23 includes corresponding bottom or second electrode holder 27 and bottom or second end piece 28.

Figure 2:
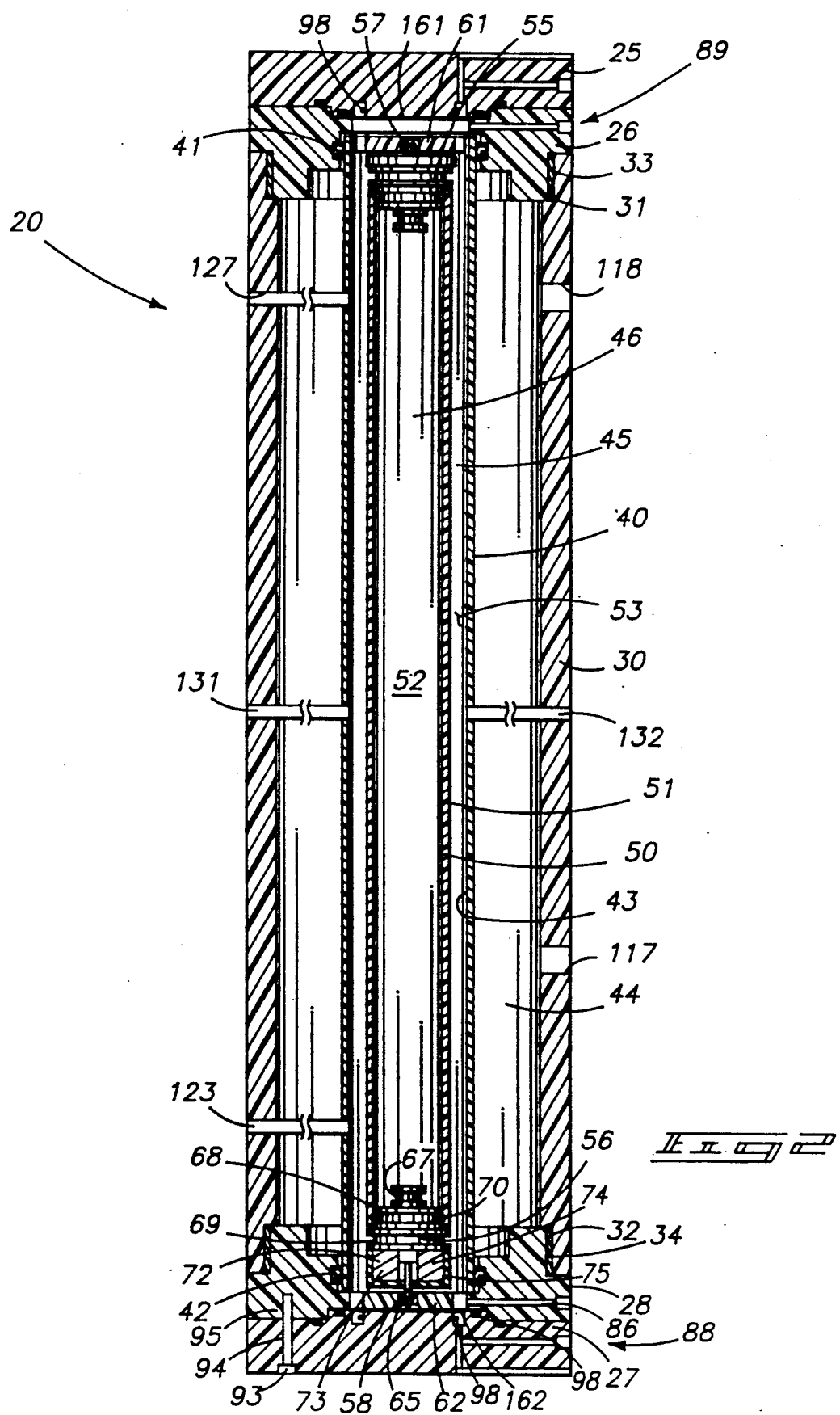
FIG. 2 is a longitudinal sectional view of principle parts of the processor of FIG. 1 taken along line 2—2 thereof.

Central section 22 includes an outer tube 30. Outer tube 30 is connected to the top and bottom end sections, specifically at end pieces 26 and 28. FIG. 2 shows this connection is advantageously provided using female threaded sections 31 and 32 formed at the upper and lower ends of outer tube 30 along the interior thereof. The female threaded sections 31 and 32 receive appropriately sized male threaded sections 33 and 34 formed on end pieces 26 and 28, respectively. The outer tube is and end sections are preferably made of PLEXIGLAS or other suitable transparent plastic material.

FIG. 2 also shows that the central section includes a stator 40 and rotor 50. Stator 40 is advantageously a tubular member having approximately cylindrical interior surfaces 43. Stator 40 is most preferably a cylindrical tube made of glass. The stator is held in a stationary position by interior bores formed within top and bottom end pieces 26 and 28. Top and bottom O-ring seals 41 and 42 are advantageously used to seal between the outer surfaces of the stator and the adjacent interior bore of the end pieces.

The outer surfaces of the stator serve to partially define a temperature stabilization chamber 44 which is formed within the outer tube 30 outside of stator 40. Outer tube 30 is preferably provided with heat transfer media communication ports 117 and 118 through which chilled water or other suitable heat transfer or cooling media can be communicated into chamber 44. Typically the temperature stabilization chamber 44 will be provided with a cooling media to remove heat dissipated within the processing chamber 45 due to Joule heating of the working fluid as current is passed therethrough between the electrodes 98. Other alternative temperature stabilization or control techniques can be utilized as is needed or appropriate.

Rotor 50 most preferably includes a tubular cylinder 52 which is held by two rotor end pieces 55 and 56 connected to the rotor tube at opposing ends thereof. The rotor tube is preferably made of glass. The rotor end pieces are preferably made of plastic, such as the preferred PLEXIGLAS.

Rotor 50 is preferably formed with approximately cylindrical exterior surfaces 51 which are juxtaposed to the interior surfaces 43 of the stator. In the preferred embodiment, the cylindrical interior surfaces of the stator and the cylindrical exterior surfaces of the rotor are spaced to provide an annular space which serves as a processing chamber 45. The radial distance between the rotor and stator is radial gap 53. The radial gap 53 is preferably approximately uniform about the rotor, although substantial variation (+ −50%) can occur while still providing operability in at least some apparatuses according to this invention. The preferred cylindrical rotor configuration defines a rotor cylinder axis which preferably coincides with the rotational axis of the rotor end pieces 55 and 56.

The rotor is preferably mounted for rotation within the stator by the rotor end pieces. FIG. 2 shows that rotor end pieces 55 and 56 are provided with pin-like rotation shafts 57 and 58, respectively, which are received within rotor mounting pieces 61 and 62. Shafts 57 and 58 are preferably made of stainless steel or other suitable material.

Figure 9:
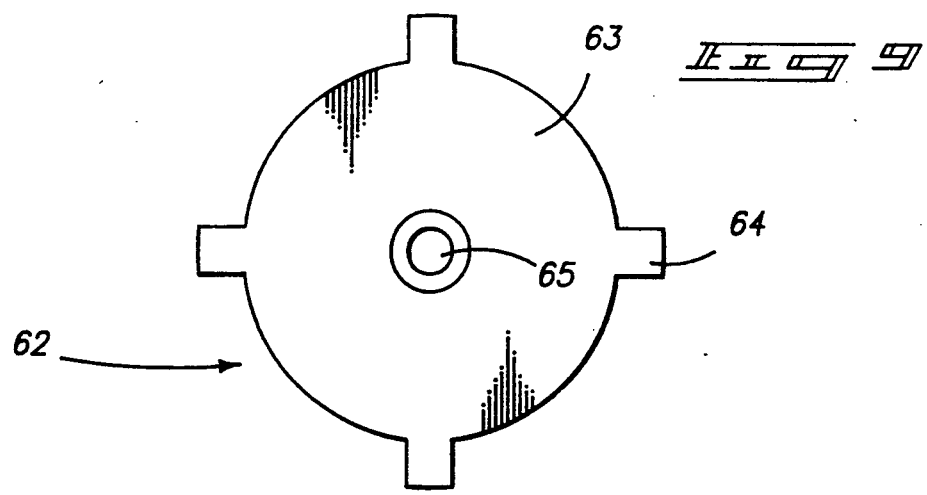
FIG. 9 is a top view of the rotor mount forming part of the processor of FIG. 1 in isolation.

FIG. 9 shows the bottom rotor mount 62 in greater detail. Rotor mount 61 is the same or substantially the same. The rotor mounts include a main part 63 which is provided with a generally circular peripheral shape. Extending from the periphery of the rotor mount main pieces 63 are a plurality of locating extensions 64. The locating extensions 64 are sized to fit within the interior of the stator, thereby radially positioning the rotor mounts therewithin. The rotor mounting pieces 61 and 62 are provided with pivot bearing inserts 65. The pin shafts 57 and 58 extending from the upper and lower rotor end pieces are received within receptacles formed in the pivot bearing inserts 65. The pivot bearing inserts are advantageously formed of stainless steel or other suitable wear and corrosion-resistant material. Remaining portions of the rotor mounts can be made of a variety of suitable plastic materials, such as the preferred PLEXIGLAS.

The rotor end pieces 55 and 56 are preferably provided with three differently sized seal grooves 67, 68 and 69. The minor diameter grooves 67 are sized to receive a small O-ring which seals with the interior diameter of a small rotor (not shown). The medium diameter grooves 68 are sized to receive O-rings 70 which seal to the interior surfaces of rotor 50. Major diameter grooves 69 are larger in diameter than grooves 67 and 68 and are sized to receive O-rings (not shown) which seal to the interior surfaces of an alternative rotor (not shown). This construction for end pieces 55 and 56 allows three different rotor sizes to be accommodated to vary the radial gap between the rotor exterior surfaces and the stator interior surfaces.

Exemplary sizes of rotors in one preferred embodiment of the invention include rotor tube sizes of 1, 1.9, and 2.2 centimeters diameter for the three different sizes. The stator inside diameter is 2.5 centimeters. The associated radial gaps between the rotor exterior surfaces and the interior surfaces of the stator are 0.75, 0.3, and 0.15 centimeter, respectively. All three rotors have similar overall lengths of approximately 25 centimeters. The outer diameter of the outer tube 30 is advantageously approximately 7 centimeters. Other sizes for the rotor, stator and outer tube are alternatively possible.

Bottom rotor end piece 56 is further advantageously adapted to allow the rotor to be driven. In the preferred embodiments shown herein, the bottom end piece is connected to a magnet assembly 72 which has a north pole 73 and south pole 74. Magnet assembly 72 preferably is encapsulated within a protective capsule 75 to prevent corrosion and electrical short circuiting. The capsule 75 can advantageously be made of silicone rubber or other suitable material. FIG. 1 shows a rotor drive in the form of an electric motor 76 and drive magnet 77 which is connected to turn with rotation of the shaft of motor 76. Rotation of drive magnet 77 causes a rotating magnetic field which applies torque to rotor magnet 72 causing rotation thereof in the same direction to form a magnetic coupling. The motor 76 and magnetic drive 77 have been omitted from FIGS. other than FIG. 1 for sake of convenience.

Processing chamber 53 between the stator and rotor is preferably provided with fluid communication ports for inflow and outflow of fluids. This is advantageously done using ports 123, 127, 131 and 132 which extend through the stator. Ports 86 and 89 extend through the end pieces to provide fluid communication at the ends of the processing chamber. In FIG. 2 the stator penetrating ports are shown for convenience as extending directly through the outer tube 30. However, it is also possible to run the connecting conduits in more lengthy arrangements within chamber 44 and have the ports open at various points, such as together in an array as illustrated solely in FIG. 1. Many alternative arrangements are possible.

Figure 3:
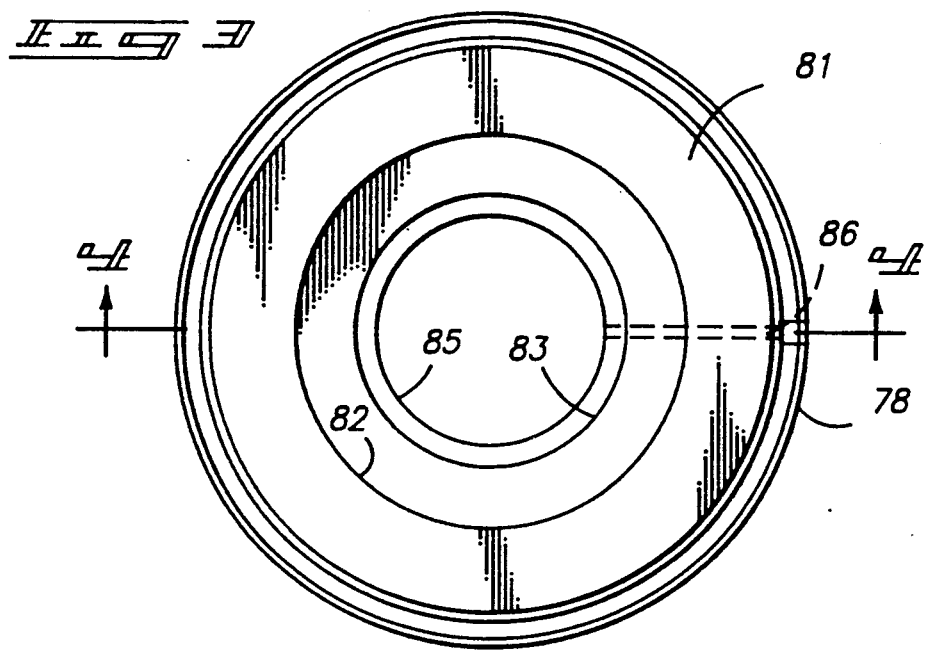
FIG. 3 is a top view of the bottom end piece forming part of the processor of FIG. 1 in isolation.
Figure 4:
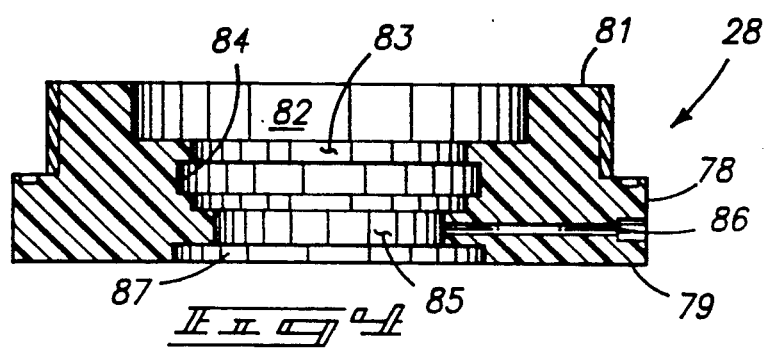
FIG. 4 is a side sectional view of the bottom end piece shown in FIG. 3 taken along line 4—4 thereof.
Figure 5:
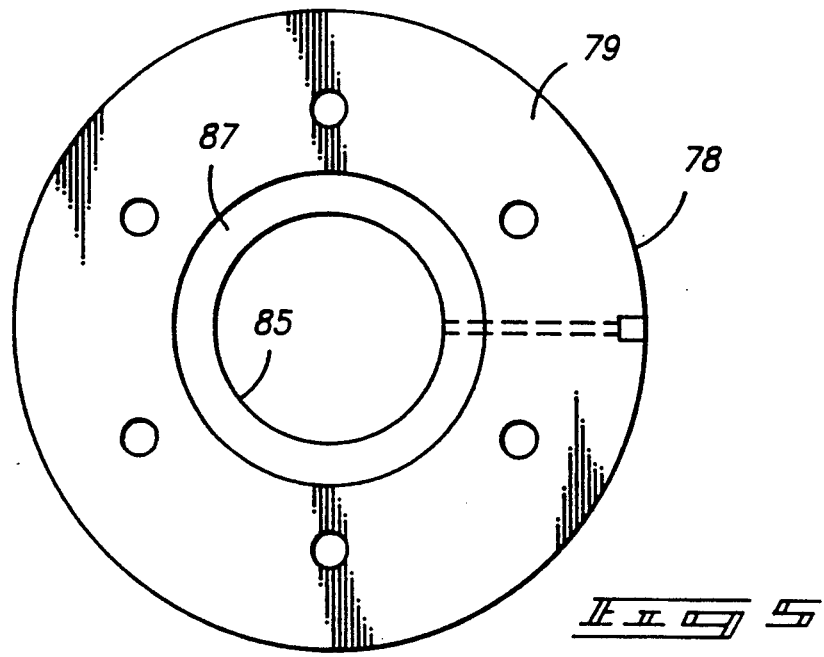
FIG. 5 is a bottom view of the bottom end piece shown in FIG. 3.

FIGS. 3-5 shows the bottom end piece 28 is greater detail. The top end piece is constructed similarly. The top and bottom end pieces 26 and 28 have exterior sidewalls 78 which extend between the distal face 79 and the flange face 80. Flange face 80 is adjacent to the threaded sections 32 and 33 explained hereinabove. Pieces 26 and 28 also include a proximal face 81 which faces inwardly toward the processing chamber. The central portions of pieces 26 and 28 include large bores 82. Adjacent to large bore 82 is a step which reduces the diameter of medium bore 83 to a size sufficient to receive the stator 40 in close proximity thereto. O-ring 42 (FIG. 2) is received within an O-ring seal groove 84 along the interior diameter of the medium bore 83. The small bore 85 of pieces 26 and 28 is approximately the same inner diameter as the inner diameter of stator 40. This provides a relatively constant inner diameter against which the rotor mount pieces 61 and 62 can fit adjacent either the small bore 85 or interior surfaces 43 of the stator.

The first and second end pieces 26 and 28 are also provided with at least one fluid passageway 86. As shown, passageway 86 extends from the outer sidewall 78 inwardly to open along the interior surface of the small bore 85. The fluid passageway 86 formed in bottom end piece 28 forms a first or bottom processing fluid access port 88. Fluid passageway 86 formed in part 26 forms a second processing fluid access port 89.

The distal faces 79 of parts 26 and 28 are advantageously provided with a membrane receptacle 87 which receive upper and lower membranes 161 and 162. Face extensions 91 (see FIG. 7) formed on the faces of the electrode holding pieces 25 and 27 extend into the membrane receptacles on the opposing sides of the membranes to provide support thereto. The membranes used in processor 20 can be of several different types. They are intended to isolate electrolyte which surrounds the electrodes 98 held in grooves 99, from the working fluid held in the processing chamber and related ports and passageways. The electrolyte facilitates the flow of current to the working fluid contained in the processing chamber. Dialysis membranes well known in the art are used when the processor is operated for zone electrophoresis separations. When the processor is used for isoelectric focusing methods, then the membrane adjacent the anode is any suitable cation-exchange membrane, and the membrane adjacent the cathode is any suitable anion-exchange membrane, both well known in the art.

FIGS. 6-8 show electrode holders 25 and 27 in greater detail. Electrode holders 25 and 27 are held in position using suitable fastening means, such as the array of six or other appropriate number of fasteners 93 which extend through fastener holds 94 and into appropriately formed receptacles 95 formed in end pieces 26 and 28. As shown, the fasteners are arranged in a regular hexagonal array about the longitudinal axis of processor 20. Fasteners 93 are preferably made from a non-ferrous and non-magnetic material, such as aluminum or magnesium, to minimize any effects on the magnetic rotor drive.

The interior faces of the electrode holders are provided with the central extensions 91 which serve to support electrode membranes 161 and 162 (see FIG. 2). An electrode 98 is received within electrode groove 99. The electrode groove 99 is semi-circular, running from a first terminus 99a to a second terminus 99b. The termini 99a and 99b are in fluid communication with axial electrolyte passages 100 and 101. Axial electrode passage 100 extends to an electrode lead groove 102 formed in the exterior face 104 of electrode holders 25 and 27. Groove 102 allows an electrode lead wire to be extended from electrode 98 outwardly and through groove 102 and across the outer sidewall 108 for connection with an electrode connection plug 106 (shown only in FIG. 6). Groove 102 is sealed with a suitable sealant such as silicone rubber after passing the electrode lead wire therethrough. This keeps fluids from passing out of passage 100. Electrode connection plug 106 is mounted within an aperture 107 formed in the sidewall 108.

The electrodes are connected to a suitable electrical power supply (not shown) which is capable of charging the electrodes to the desired voltages and providing sufficient current through the processing chamber. A variety of power supplies now used in electrophoretic systems can be used. The typical voltage ranges are 1000-2000 volts across the electrodes. This establishes and electrical field having a field gradient which extends over a distance of approximately 25 centimeters in the preferred embodiment described herein. The current requirements of the power supply will vary dependent upon the processing fluid. Typically power supplies capable of delivering variable or constant current outputs up to approximate 1 amp at the indicated voltages will be appropriate for use in this invention.

The axial electrolyte passageway 100 also connects with a first electrolyte radial passage 110. Similarly, axial passageway 101 connects with a second radial electrolyte passage 111. In preferred operating modes, electrolyte can be circulated through the electrolyte groove 99 by forcing it in and out through passageways 110, 100, 99, 101 and 111 in either direction.

When processor 20 is used in zone electrophoresis modes of operation, then the electrode electrolyte can be a range of suitable fluids, most easily the buffer solution typically used as the working fluid. In the isoelectric focusing mode of operation, the anode electrolyte should be a relatively strong acid solution, e.g. 0.1M phosphoric acid, and the cathode electrolyte should be a relatively strong basic solution, e.g. 0.1M sodium hydroxide. Many other alternative electrolytes can be used.

The outer ends of radial electrolyte flow passageways 110 and 111 form electrolyte ports which are advantageously provided with fittings (not shown). Tubing is connected to the fittings for conveying the electrolyte from a suitable source and to a suitable disposal or recycle system (not shown) as desired in the particular processing system.

The interior faces 103 of electrode holders 25 or 27 are each advantageously provided with an O-ring groove 112 which receives an O-ring 113. The inner portion of interior face 103 associated with extension 91 is similarly provided with an O-ring groove 114 and associated sealing O-ring 115. O-rings 113 seal against the outward or distal faces of the end pieces 26 and 28. O-rings 115 seal against the electrode membranes 161 and 162.

FIGS. 10 and 10A show an alternative electrophoretic processor 220 according to this invention. Processor 220 is similar to processor 20 described elsewhere herein. Parts similar to both processors 20 and 220 are referenced using the same reference numerals to simplify the description. Processor 220 differs from processor 20 only with respect to the features described below.

Processor 220 additionally includes a movable catheter 230 which is slidably received within a catheter aperture 231 formed through the top electrode holder 25. Catheter aperture 231 is positioned to allow the catheter 230 to be extended between extensions 64 on the top rotor mount 61. The catheter aperture is also aligned parallel to the longitudinal axis of the annular processing chamber 45 and at a radial position appropriate to allow extension along a line just inwardly from the interior surface 43 of stator 40. This construction allows extension of the distal end of the catheter into the processing chamber to varying depths to permit extraction of desired isoelectrically focused components of the fluid being processed.

The catheter aperture is preferably provided with an appropriate seal for slidably sealing about the catheter and between the electrode holder. As shown the catheter seal is provided in the form of an O-ring 232 held within an O-ring groove 233. The catheter is advantageously a metal tube of small diameter and high strength to allow repeated insertion and removal. For purposes of illustration catheter 230 is shown condensed in length; however, it is desirably of sufficient length to allow removal of any fraction contained within the processing chamber.

FIG. 11 shows a further alternative embodiment electrophoretic processor 320 according to this invention. Processor 320 is similar to processor 20 described elsewhere herein. Parts similar to both processors 20 and 320 are referenced using the same reference numerals to simplify the description given herein. Processor 320 differs from processor 20 only with respect to the features described below.

The stator 40 in processor 320 is provided with an array of spaced product ports 321–345. Ports 321–345 are advantageously provided with associated conduits which connect the ports through the outer tube 30 to allow extraction of the fractions developed during isoelectric focusing electrophoresis, as explained more fully hereinafter.

Systems, Operation and Methods

The processors 20, 220 and 320 described herein can be operated in a number of different operational modes to effectuate novel processes according to this invention. The preferred operational modes include batch and continuous zone electrophoretic separation, and isoelectric focusing separation. In zone electrophoresis the electrophoretically mobile chemicals are processed in a working fluid having an approximately uniform pH. Molecules having different electrophoretic mobilities move through the working fluid at different rates dependent upon geometry, size, and the charge of the molecules. Isoelectric focusing is explained in greater detail below after explanation of the continuous and batch zone electrophoresis processing.

Figure 12:
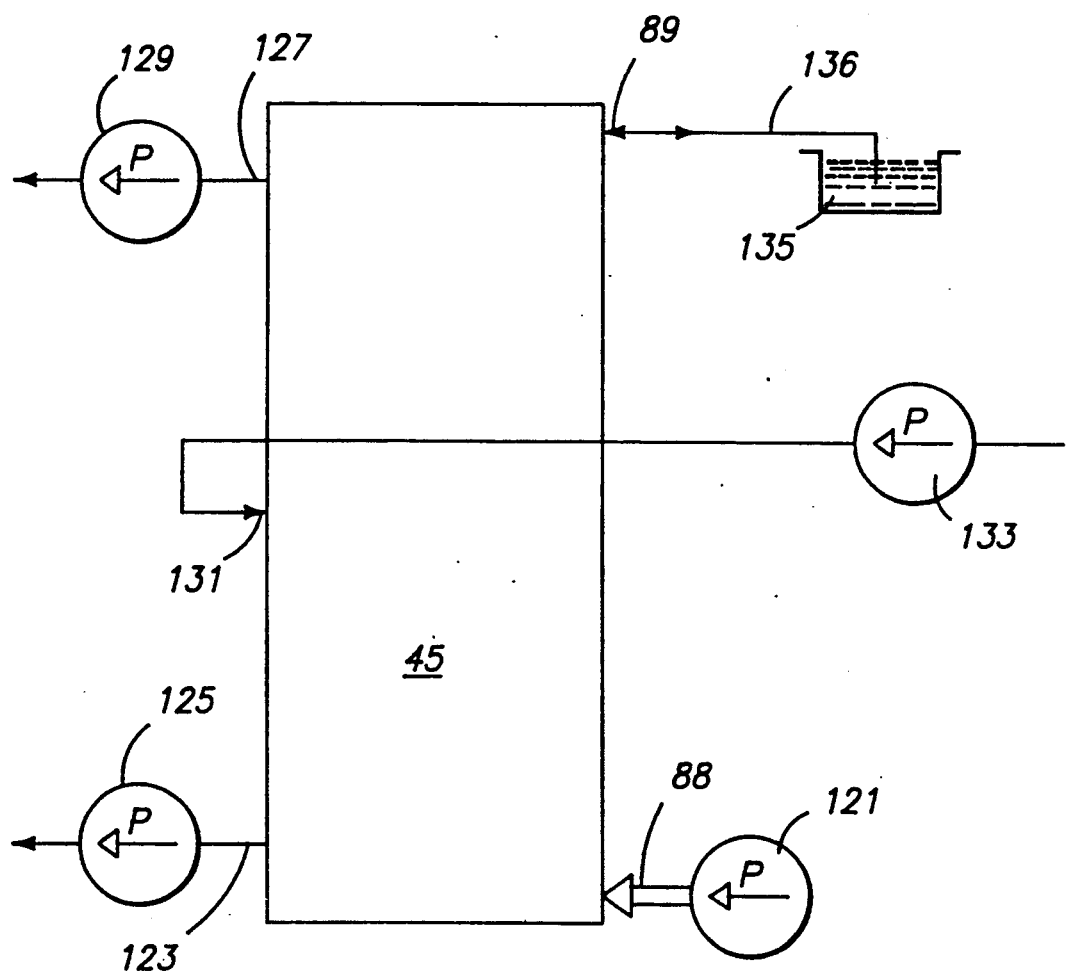
FIG. 12 is a schematic view showing the processor of FIG. 1 connected in a processing system useful in performing methods as explained in greater detail herein.

FIG. 12 shows a schematic representation of the processing chamber 45 of processor 20. Processor 20 is connected to allow continuous flow zone electrophoretic separation of two or more chemical fractions having different electrophoretic mobilities. The processing is preferably accomplished in the liquid phase using a working fluid. Examples of suitable working fluids include fluids such as electrophoresis buffer solutions suitable for the chemical system being processed. Such electrophoresis buffer solutions are well known in the art of free fluid electrophoretic separation. The flow of working fluid in through port 88 causes a working fluid flow within the process chamber 45 which is in opposition to the direction of molecule migration under the force of the electric field. The polarity of the electrodes 98 depends upon whether the molecules being separated assume negative or positive charges during electrophoresis in the working fluid selected.

The primary working fluid inlet port to the processing chamber 45 is bottom end piece fluid access port 88. A working fluid is supplied to port 88, such as by using pump 121. Pump 121 is advantageously a peristaltic tubing pump. The working fluid from pump 121 passes through port 88 and into the bottom portion of the processing chamber. The primary countercurrent working fluid flow supplied through port 88 is greater in rate than the flow rates of other individual flows into or from processing chamber 45. This establishes the counter-mobility fluid flow within the processing chamber. In preferred operation the counter-mobility working fluid flow is longitudinal in general direction, from bottom to top of the annular processing chamber 45.

A higher mobility outlet port 123 is positioned near but above the lower end of the processing chamber. In the preferred processor 20 about 2.5 centimeters above the lower end of the processing chamber. Port 123 removes about one half of the primary working fluid flow supplied by pump 121. The outflow through port 123 is induced by higher mobility outflow pump 125. The outflow at port 123 causes a substantial velocity decrease in the upwardly flowing working fluid. The greater velocity below port 123 in the lower terminating section of the processing chamber tends to sweep even the most mobile charged molecules upwardly to the level of port 123. The slower velocity above port 123 allows the higher mobility molecules to transit downwardly due to greater electrokinetic force than the hydrodynamic drag of the working fluid. Pump 125 is advantageously a peristaltic tubing pump, and can most conveniently be operated on a common peristaltic pump drive shaft with pump 121 to best coordinate the primary inflow and higher mobility port outflow rates.

FIG. 12 also shows a lower mobility outlet port 127 which is near but removed from the upper end of the processing chamber. In the preferred processor 20 about 2.5 centimeters below the upper end of the processing chamber. Outflow through port 127 is controlled by a lower mobility outflow pump 129. Pump 129 is also preferably a peristaltic tubing pump driven on a common drive with pumps 121 and 125. The lower mobility outflow rate is most preferably about equal to the higher mobility outflow rate, both equal to approximately one-half of the primary inflow rate provided by pump 121. The flow of fluid above port 127 will typically be small thus providing little or no effective counterflow drag on the charged molecules. This allows even molecules of very low mobility to transit downwardly in the upper terminating section of the processing chamber.

The sample containing the electrophoretically mobile molecules is advantageously fed through the sample feed inlet port 131 using a sample supply pump 133 and associated feed stream conduit 132. Pump 133 can advantageously be a syringe-type pump, well known in the art, or other suitable pump type. The sample is typically fed with the mobile chemicals in solution with the working fluid or other appropriate solute.

The system of FIG. 12 also includes means for balancing the fluid flows to and from the processing chamber 45. This fluid flow balancing means is advantageously in the form of a reservoir 135 containing a supply of working fluid therein. A conduit 136 extends from the upper end processing fluid access port 89 and beneath the level of the working fluid contained in reservoir 135. This arrangement allows working fluid to either be taken in or expelled from the processing chamber through port 89 as the other fluid flows to and from the processing chamber may require on an instantaneously changeable basis.

The system of FIG. 12 can be used to continuously process a feed stream containing molecules of differing electrophoretic mobilities to separate the feed stream into two fractions based upon mobility. The process includes feeding the feed stream into an approximately annular processing chamber, such as processing chamber 45. The feed stream must be fed at an appropriate rate when using a system as shown in FIG. 12. If the feed stream rate is too large, then the velocity above the feed port 131 in the upper product section of the chamber will potentially be too great to allow even the more mobile molecules to pass counter-currently downward. This limitation on feed rate can be remedied using the system of FIG. 13 as will be explained more fully below. The particular limitations on feed rate depend upon a variety of factors which are specific to the processor geometry and chemical system being used.

The process further includes establishing an electrical field having a voltage gradient which varies along the longitudinal length or axis of the annular processing chamber. The electrical field strength can vary over a wide range of values as is well known in the art of electrophoretic processing. Typically the field strength will be in the range of 20–100 volts per centimeter. In general with the preferred processors described herein, the electrodes are charged to voltages which provide a differential voltage therebetween which are typically in the range of 1000–2000 volts.

The process also includes inducing a transverse secondary flow of the process fluid. This inducing step is significant in improving heat transfer and reducing the ill effects of electroosmosis which tends to create longitudinal fluid currents in the process fluid along the chamber surfaces. These ill effects are caused by electrical charge development along the surfaces of the processing chamber, as is recognized and described in the art.

The inducement of a transverse secondary flow is preferably accomplished by rotating a rotor, such as rotor 50, having surfaces which at least partially define the processing chamber. The rotational speed is of sufficient magnitude to induce a transverse secondary flow of the process fluid which reduces the longitudinal migration of mobile molecules contained therein. The rotation is preferably done at sufficient rotational velocity to induce toroidal laminar secondary flow cells which are called Taylor vortices.

Figure 15:
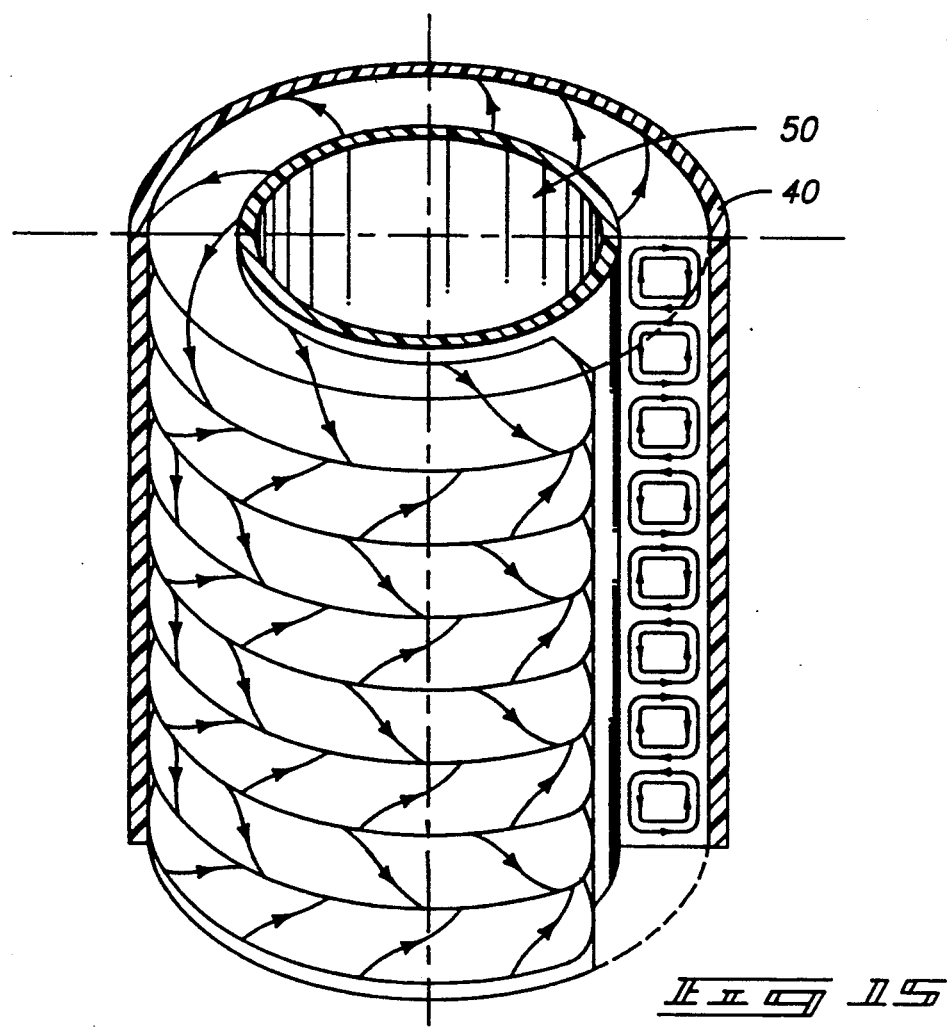
FIG. 15 is a diagram generally showing the toroidal secondary flows or Taylor vortices preferably developed by the processor.

Taylor vortices are diagrammatically shown in FIG. 15. The toroidal vortices spiral transversely between the stator and rotor at a plurality of longitudinal positions. Each Taylor vortex cell is approximately square in cross-sectional size as determined by the annular processing chamber gap size 53. A circulating laminar flow of processing fluid spirals through the cell as illustrated in a spiraling donut appearance.

The angular speeds needed to generate the Taylor vortices varies dependent upon fluid properties (primarily kinematic viscosity), process chamber gap, and radius of the inner cylinder. This has been represented in theoretical work on Taylor vortex development. The flow conditions relevant to Taylor vortex development are represented by the Taylor number, T, which is defined as:

$$T = (4\pi^2 f^2 R^5)/\nu^2 d$$

where: f is the rotational frequency; R is the radius of the inner cylinder; $\nu$ is the kinematic viscosity; and d is the annular gap. Flows having Taylor numbers within a critical range typically induce Taylor vortices. The lower critical Taylor number, $T_c = 1708$, results in the generation of Taylor vortices. The upper critical Taylor number is approximately 3025. Both of these numbers apply to the preferred embodiment geometry and sizes set forth in this application.

Figure 14:
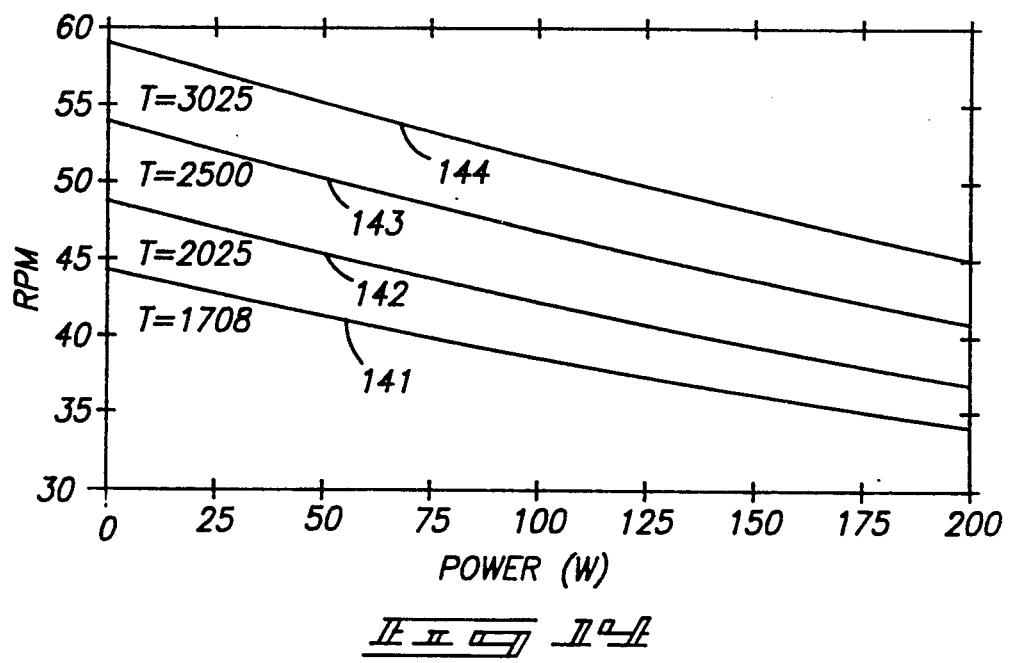
FIG. 14 is a graph showing rotor angular velocities used to achieve Taylor vortices as a function of power input to the system.

FIG. 14 is a graph showing appropriate Taylor numbers on the lines labeled 141–144. The corresponding Taylor numbers are 1708, 2025, 2500, and 3025, respectively. Taylor vortices are typically formed with a processor of the type and size described above when the Taylor numbers range from approximately 1708 to 3025. At Taylor numbers below 1708 the flow does not typically develop into the characteristic toroidal vortex and a Couette flow regime is established which is not as effective for use in the processing described herein. At Taylor numbers above 3025 the flow typically becomes turbulent. Turbulent flow is undesirable because it causes excessive mixing and prevents the desired separation. Thus the inducing and rotating processing steps can be effectively accomplished by rotating at an appropriate angular speed to create transverse toroidal secondary flows of the Taylor vortex type.

For a variety of processor geometries, the preferred rotational speeds are typically in the range of 10–400 revolutions per minute, more preferably 30–100 revolutions per minute.

The processing advantageously accomplished by the system illustrated by FIG. 12 also includes flowing a counterflow of processing fluid or other working fluid through the processing chamber in a direction generally longitudinal and in opposition to migration of at least one of the electrophoretically mobile chemicals contained in the process fluid. This is advantageously accomplished by pumping a suitable buffer into the processing chamber, such as through the primary working fluid port 88. The counterflowing fluid preferably moves from the bottom of the annular processing chamber upwardly. The counterflow of fluid through the processing chamber is at a rate appropriate to sweep the less mobile molecules upwardly against the electrical field established. The counter flow is also preferably at a rate appropriate to allow the more mobile molecules to move downwardly along the processing chamber as forced by the electrical field produced, such as by electrodes 98.

The zone focusing electrophoretic processes of this invention also preferably involve varying the counterflow velocity along the length of the processing chamber. The velocity changes along the processing chamber allow the counterflow to selectively sweep molecules of a given mobility to a desired position or zone. The velocity change at a particular point is effected by outflowing a portion of the counterflow, such as by outflowing at higher mobility port 123. The velocity between port 123 and port 131 thus is approximately constant and of a speed which allows the higher mobility molecules to move to port 123. However, the velocity between ports 123 and 131 is high enough to prevent the lower mobility molecules which are being separated from progressing to port 123.

The counterflow velocity between port 131 and 127 can be either greater than or equal to the velocity between ports 123 and 131. During continuous flow operation the feed port supplies fluid and the velocity between ports 131 and 127 will be higher on average than the velocity between ports 123 and 131. This is an undesirable velocity profile but is acceptable for simplicity purposes. The higher velocity in the upper section is acceptable until it prevents the more mobile molecules from being forced by the electrical field between ports 127 and 131. Under such conditions the sample feed flow rate must be reduced or an alternative system used as explained below.

Figure 13:
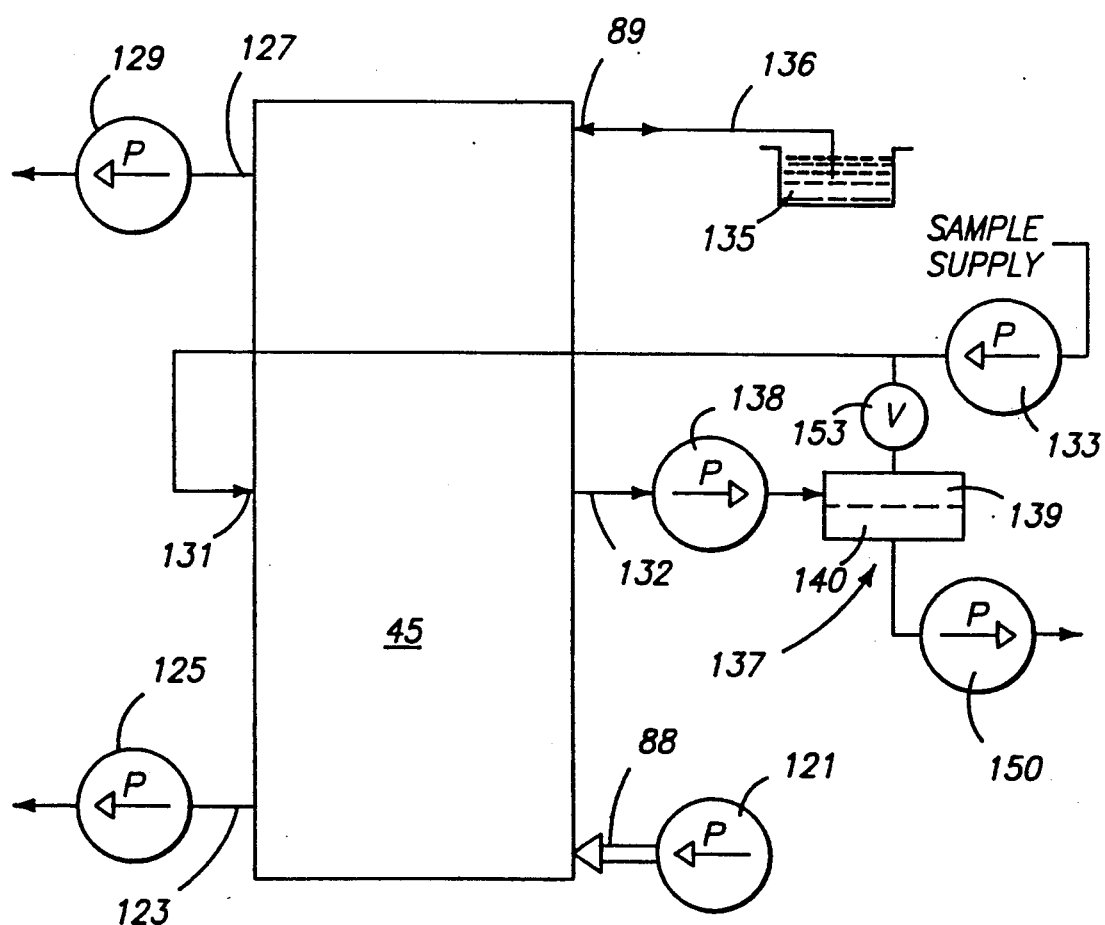
FIG. 13 is a schematic view showing the processor of FIG. 1 connected in a processing system useful in performing methods as explained in greater detail herein.

FIG. 13 shows an alternative system which is provided with additional components which remedy the potential problems associated with a significantly higher counterflow velocity in the upper section of the processing chamber. The system of FIG. 13 is similar to that shown and described with respect to FIG. 12 and the same reference numerals have been used for similar parts. The system of FIG. 13 also includes an infeed recycle port 132 which is positioned along approximately the same longitudinal position as the feed port 131. A feed recycle pump 138 is used to control the recycle flow rate out through port 132. Pump 138 is also preferably a peristaltic tubing pump. The outlet of pump 138 is fed to the first side 139 of an ultrafilter 137. Ultrafilter 137 is of sufficiently small pore size so as to retain the molecules which are being separated. The second side 140 of filter 137 is connected to a pump 150 which is used to remove sufficient working fluid from the recycle line to effectuate the desired net flow increase, decrease or equality desired at the medial section of the processing chamber. The net flow is decreased by removing with pump 150 fluid at a rate in excess of the sample feed rate provided by pump 133. The converse applies if a net flow increase is desired. If no net effect is desired then the flows through ports 131 and 132 are balanced.

The velocity in the upper section of the processing chamber can thus be adjusted by varying the feed inflow through port 131 and the feed recycle outflow which occurs through port 132. If these flows are made equal, then the processing chamber longitudinal counterflow velocity is equal between ports 123 and 127. If there is a net outflow at the feed section then the counterflow velocity above ports 131 and 132 is generally decreased. If there is a net inflow, then the counterflow velocity above ports 131 and 132 increases as was the case in the system of FIG. 12.

The novel processes for continuous electrophoretic separation processing further include removing at least two outflow streams containing the fractions being separated. This is advantageously done through the upper and lower product ports 127 and 123 which carry the relatively low mobility and high mobility fractions, respectively.

EXAMPLE 1

Continuous flow zone electrophoretic processing was performed in a processor as described above in connection with processor 20. Chilled water at 2° C. was used as cooling media and circulated through the cooling jacket chamber 44. The medium size rotor was employed. A mixture of approximately 1% bovine albumin and 1% bovine hemoglobin in an aqueous buffer solution was prepared using commercial sources of these chemicals. The buffer solution was 20 mM tris-acetate at pH 8.0. The albumin was rendered visible by dyeing with bromophenol blue prior to injection into the processing chamber. The mixture was fed at a rate of 15 milliliters per hour using a system similar to that shown in FIG. 12. The counterflow of buffer was approximately 40 milliliters per hour. The electrodes were charged to a differential voltage of 1350 volts. The albumin separated as the higher mobility product through port 123 and the hemoglobin separated as the lower mobility product through port 127. No cross-contamination was detected in either resulting product stream.

The invention further includes processes for batch electrophoretic separation of chemical constituents having differing electrophoretic mobilities. The batch electrophoretic zone processing described herein is not a true batch process in that a working fluid, such as a buffer, is counterflowed through the processing chamber. However, the reference to batch processing relates to the use of a single sample charge which is fed into the processing chamber in a charging operation. The electrophoretic zone processing then proceeds with time upon the sample charge to separate the electrophoretically mobile components in one or more zones along a counterflow having a varying velocity profile.

The batch electrophoretic zone processing can be performed using the system illustrated in FIG. 13. The process includes feeding an approximately annular processing chamber, such as processing chamber 45. The feeding is performed upon a fixed sample over a period of time to thereby perform charging of the processing chamber with the sample and any suitable carrier fluid in which the sample is carried. Feeding and charging of the sample is accomplished in the system of FIG. 13 by pumping the sample using pump 133 and feeding the sample fluid into the processing chamber 45 through the sample infeed port 131. The sample charging is preferably done while also counterflowing the working fluid through the processing chamber as described hereinabove.

The batch zone processes of this invention further include establishing an electrical field as described hereinabove in connection with the continuous flow zone electrophoresis separation processes. Similarly, the rotating and inducing of secondary flows are similar to those described above.

The batch zone processes further include varying the counterflow velocity along the length or longitudinal axis of the processing chamber to focus at least one of the mobile chemicals within a zone. The zone or zones are typically provided at a position along the processing chamber whereat the counterflow velocity changes due to the removal of working fluid. For example, at the medial position where fluid can be removed at the recycle port 132 using pump 138 and 150. In such an operation a flow restricting valve 153 can be included to separate the feed port 131 and removal port 132. In this operation the processing chamber is thus provided with a velocity profile which decreases upwardly. The final step of velocity decrease is between the upper product port 127 and port 89 wherein the velocity becomes very low and the electrical field tends to move all mobile constituents of the process fluid downwardly.

The batch zone processing tends to focus the desired protein or other chemical in a desired zone. For example the system can be operated to focus a single constituent being sought along the medial section. After sufficient time has passed for the desired constituent to be separated into the medial zone, then the process further includes removing fluid from the zone of the processing chamber to obtain the chemical fraction which has been separated. Thus the processing chamber is charged with the initial sample containing a variety of constituents and the processed fluid retains the single or multiple constituents desired having appropriate mobilities to selectively retain or focus them at the point in the processing chamber at which electric field mobility and counterflow velocity are in balance.

EXAMPLE 2

Batch zone electrophoretic processing was performed in a processor as described above in connection with processor 20. Chilled water at 2° C. was used as cooling media and circulated through the cooling jacket chamber 44. The medium size rotor was employed. A mixture of approximately 1% bovine albumin and 1% bovine hemoglobin in an aqueous buffer solution was prepared using commercial sources of these chemicals. The buffer solution was 20 mM tris-acetate at pH 8.0. The albumin was rendered visible by dyeing with bromophenol blue prior to injection into the processing chamber. The mixture was fed at a rate of 23.2 milliliters per hour using a system similar to that shown in FIG. 13. Recycle flow from port 132 was 19.6 milliliters per hour. The net feed was 3.6 milliliters per hour. The sample was fed during an initial charging period of about 20 minutes duration. The counterflow of buffer was varied from approximately 60 milliliters per hour to 100 milliliters per hour during the period of separation. The electrodes were charged to a differential voltage of approximately 1600 volts. The albumin was separated into the medial zone as the higher mobility product. The hemoglobin separated as the lower mobility product exiting through port 127 in the counterflow stream. The batch separation process proceeded for about 3 hours. The albumin containing process liquid was removed by draining the processing chamber.

The processors of FIGS. 10 and 11 are specifically adapted to facilitate operation in an isoelectric focusing mode of operation and description of this mode of operation will be made with reference to these FIGS. The isoelectric focusing mode of operation includes charging processing chamber 45 with a isoelectric process fluid containing at least two chemicals which have differing electrophoretic mobilities. These chemicals are often proteins or can alternatively be other electrophoretically mobile components being separated. The isoelectric process fluid also contains a suitable ampholyte mixture which causes a pH gradient to be established in response to the voltage gradient applied when the electrodes 98 are charged to the desired differential voltages.

The isoelectric focusing modes and methods also include establishing an electrical field having a voltage gradient varying along said longitudinal axis of the processing chamber 45. The electrical field established can be of either polarity. Establishing the electrical field within the ampholyte containing isoelectric process fluid results in creating a pH gradient having a range of pH conditions within the processing chamber fluid. Creating a pH gradient within the processing chamber fluid chamber allows the electrophoretically mobile chemical constituents of the isoelectric processing fluid to separate at different longitudinal positions where the pH is equal to the isoelectric point of the particular constituent.

The separating step is preferably accomplished while rotating the rotor 40. Rotor 40 is preferably rotated at angular speeds sufficient to generate annular Taylor vortices in the processing chamber for the particular rotor size being employed. The developing or generating of the annular Taylor vortices helps to prevent electroosmosis during processing, improves heat transfer with the stator and rotor to allow heat removal or other temperature stabilization. Generating Taylor vortices also helps to prevent vertical convection currents from developing. Convection currents which can otherwise develop are derogatory to the isoelectric focusing of the constituent chemicals at the appropriate isoelectric pH location. The Taylor vortices generated help prevent large scale convective currents from mixing the isoelectric process fluid and maintain focused bands in relatively homogeneous condition.

In this approach the electrodes 98 are charged to the desired potentials using any power supply suitable to generate the desired voltages at the electrodes and maintain the electrodes at the desired differential voltages as current flows between the electrodes across the processing chamber. Such current flows as a result of the pressure of charge carriers in the processing fluid.

In general the polarity of the chemicals being electrophoresed and the polarity of the electrical field established by electrodes 98 is coordinated so that the electrical field force exerted upon the chemicals is downward in the processors described herein.

EXAMPLE 3

Batch isoelectric electrophoretic processing was performed in a processor as described above in connection with processor 20. Chilled water at 2° C. was used as cooling media and circulated through the cooling jacket chamber 44. The medium size rotor was employed. A sample containing 10 milligrams of bovine albumin and 10 milligrams bovine hemoglobin in an aqueous buffer solution was prepared using commercial sources of these chemicals. The albumin was rendered visible by dyeing with bromophenol blue prior to injection into the processing chamber. The buffer solution was formed from deionized water and contained 2% Pharmalyte 3-10 ampholyte mixture (Pharmacia Brand). The albumin and hemoglobin were mixed with approximately 60 milliliters of such buffer and the resulting process fluid was fed into the processing chamber by pumping in from the bottom using a pump such as pump 121 described in FIGS. 12 and 13. The power supply was operated in the constant power mode at 100 watts. The initial voltage was 1000 volts. The separation processing was performed for approximately 45 minutes. Each constituent formed a band or zone approximately 2.4 centimeters high. A central band or zone approximately 6 centimeters high without color was present between the focused bands of protein. The zones of protein had estimated mean concentrations of 0.2% protein. More concentrated zones within the broader bands were estimated to have protein concentrations of approximately 1%.

In compliance with the statute, the invention has been described in language necessarily limited in its ability to properly convey the conceptual nature of the invention. Because of this inherent limitation of language, it must be understood that the invention is not necessarily limited to the specific features described, since the means herein disclosed comprise merely preferred forms of putting the invention into effect. The invention is, therefore, claimed in any of its forms or modifications within the proper scope of the appended claims appropriately interpreted in accordance with the doctrine of equivalents.

We claim:

1. An electrophoretic processor comprising:
   a stator;
   a rotor mounted for rotation about an axis of rotation;
   a rotor drive for rotating said rotor;
   a processing chamber at least partially defined between the stator and rotor;
   a first electrode positioned adjacent a first end of the processing chamber;
   a second electrode positioned adjacent a second end of the processing chamber;
   at least one ion exchange electrode membrane for separating at least one of said first or second electrodes from the processing chamber;
   at least one fluid access port allowing fluid communication to or from said processing chamber.

2. An electrophoretic processor according to claim 1 wherein there are a plurality of fluid access ports.

3. An electrophoretic processor according to claim 1 wherein rotor size is adjustable to provide various sized spacings between the stator and the rotor.

4. An electrophoretic processor comprising:
   a stator;
   a rotor mounted for rotation about an axis of rotation;
   a rotor drive for rotating said rotor;
   a processing chamber at least partially defined between the stator and rotor;
   a first electrode positioned adjacent a first end of the processing chamber;
   a second electrode positioned adjacent a second end of the processing chamber;
   at least one fluid access port allowing fluid communication to or from said processing chamber;
   a moveable catheter slidably mounted in substantially sealed relationship with the processing chamber for extracting fluid from a plurality of locations within the processing chamber.

5. An electrophoretic processor according to claim 4 wherein rotor size is adjustable to provide various sized spacings between the stator and the rotor.

6. An electrophoretic processor comprising:
   a stator;
   a rotor mounted for rotation about an axis of rotation;
   a rotor drive for rotating said rotor, said rotor drive being a magnetic coupling;
   a processing chamber at least partially defined between the stator and rotor;
   a first electrode positioned adjacent a first end of the processing chamber;
   a second electrode positioned adjacent a second end of the processing chamber;
   at least one fluid access port allowing fluid communication to or from said processing chamber.

7. An electrophoretic processor according to claim 6 wherein there are a plurality of fluid access ports.

8. An electrophoretic processor according to claim 6, wherein rotor size is adjustable to provide various sized spacings between the stator and the rotor.

9. An electrophoretic processor comprising:
   a stator having interior surfaces which are approximately cylindrical about a stator cylinder axis;
   a rotor having exterior surfaces which are approximately cylindrical about a rotor cylinder axis; said rotor being mounted within the stator for rotation about an axis of rotation which approximately coincides with the stator cylinder axis and the rotor cylinder axis;
   a rotor drive for rotating said rotor;
   a processing chamber at least partially defined between the stator and rotor;
   a first electrode positioned adjacent a first end of the processing chamber;
   a second electrode positioned adjacent a second end of the processing chamber;
   at least one ion exchange electrode membrane for separating at least one of said first or second electrodes from the processing chamber;
   at least one fluid access port allowing fluid communication to or from said processing chamber.

10. An electrophoretic processor according to claim 9 wherein rotor size is adjustable to provide various sized spacings between the stator and the rotor.

11. An electrophoretic processor comprising:
    a stator having interior surfaces which are approximately cylindrical about a stator cylinder axis;
    a rotor having exterior surfaces which are approximately cylindrical about a rotor cylindrical axis; said rotor being mounted within the stator for rotation about an axis of rotation which approximately coincides with the stator cylinder axis and the rotor cylinder axis;
    a rotor drive for rotating said rotor;
    a processing chamber at least partially defined between the stator and rotor;
    a first electrode positioned adjacent a first end of the processing chamber;
    a second electrode positioned adjacent a second end of the processing chamber;
    at least one fluid access port allowing fluid communication to or from said processing chamber;
    a moveable catheter slidably mounted in substantially sealed relationship with the processing chamber for extracting fluid from a plurality of locations within the processing chamber.

12. An electrophoretic processor according to claim 11 wherein there are a plurality of fluid access ports.

13. An electrophoretic processor according to claim 11 wherein rotor size is adjustable to provide various sized spacings between the stator and the rotor.

14. An electrophoretic processor comprising:
    a stator having interior surfaces which are approximately cylindrical about a stator cylinder axis;
    a rotor having exterior surfaces which are approximately cylindrical about a rotor cylinder axis; said rotor being mounted within the stator for rotation about an axis of rotation which approximately coincides with the stator cylinder axis and the rotor cylinder axis;
    a rotor drive for rotating said rotor, said rotor drive being a magnetic coupling;

a processing chamber at least partially defined between the stator and rotor;
a first electrode positioned adjacent a first end of the processing chamber;
a second electrode positioned adjacent a second end of the processing chamber;
at least one fluid access port allowing fluid communication to or from said processing chamber.

15. An electrophoretic processor according to claim 14 wherein there are a plurality of fluid access ports.

16. An electrophoretic processor according to claim 14 wherein rotor size is adjustable to provide various sized spacings between the stator and the rotor.

17. A process for electrophoretically processing, comprising:
charging an approximately annular processing chamber with a fluid containing at least two chemicals which have differing electrophoretic mobilities; said fluid also containing at least one ampholyte which causes pH to vary dependent upon an electrical field voltage gradient; said annular processing chamber having a longitudinal axis and a first end and a second end spaced along said longitudinal axis;
establishing an electrical field having a voltage gradient varying along said longitudinal axis of the processing chamber; said voltage gradient thereby producing a range of pH conditions within the fluid contained within the processing chamber;
rotating a rotor having surfaces which partially define the annular processing chamber to thereby induce rotational flow in said fluid within the processing chamber;
separating said at least two chemicals contained in said fluid at various approximate longitudinal positions within the processing chamber;
extracting said at least two chemicals from the processing chamber by removing fluid from the processing chamber at differing longitudinal positions along the processing chamber.

18. A process according to claim 17 and further defined by said rotating being at an angular speed sufficient to induce a plurality of annular vortices at spaced locations along said longitudinal axis.

19. A process according to claim 17 and further defined by said rotating being at an angular speed in excess of 10 revolutions per minute.

20. A process according to claim 17 and further defined by:
maintaining outer surfaces of the approximately annular processing chamber stationary; and
said rotating being accomplished by rotating a rotor defining inner surfaces of the approximately annular processing chamber.

21. A process according to claim 17 and further defined by providing an annular processing chamber not obstructed with transverse dividers along the longitudinal axis thereof.

22. A process for electrophoretically processing, comprising:
charging an approximately annular processing chamber with a fluid containing at least two chemicals which have differing electrophoretic mobilities; said fluid also containing at least one ampholyte which causes pH to vary dependent upon an electrical field voltage gradient; said annular processing chamber having a longitudinal axis and a first end and a second end spaced along said longitudinal axis;
establishing an electrical field having a voltage gradient varying along said longitudinal axis of the processing chamber; said voltage gradient thereby producing a range of pH conditions within the fluid contained within the processing chamber;
rotating a rotor having surfaces which partially define the annular processing chamber to thereby induce rotational flow in said fluid within the processing chamber;
separating said at least two chemicals contained in said fluid at various approximate longitudinal positions within the processing chamber;
extracting said at least two chemicals from the processing chamber by removing fluid from the processing chamber at a plurality of longitudinal positions along the processing chamber.

23. A process according to claim 22 and further defined by said rotating being at an angular speed sufficient to induce a plurality of annular vortices at spaced locations along said longitudinal axis.

24. A process according to claim 22 and further defined by said rotating being at an angular speed in excess of 10 revolutions per minute.

25. A process according to claim 22 and further defined by:
maintaining outer surfaces of the approximately annular processing chamber stationary; and
said rotating being accomplished by rotating a rotor defining inner surfaces of the approximately annular processing chamber.

26. A process according to claim 22 and further defined by providing an annular processing chamber not obstructed with transverse dividers along the longitudinal axis thereof.

27. A process for electrophoretically processing, comprising:
feeding an approximately annular processing chamber with a fluid containing at least two chemicals which have differing electrophoretic mobilities; said annular processing chamber having a longitudinal axis and a first end and a second end spaced along said longitudinal axis;
establishing an electrical field having a voltage gradient varying along said longitudinal axis of the processing chamber;
rotating a rotor having surfaces which partially define the annular processing chamber to thereby induce rotational flow in said fluid within the processing chamber;
flowing a counterflow liquid through the processing chamber in a longitudinal direction generally in opposition to migration of at least one of said chemicals;
varying the velocity of the counterflow liquid along the longitudinal axis of the processing chamber to focus at least one of said chemicals within a zone;
removing fluid from said zone to obtain at least one of said chemicals in a form separated from at least another chemical contained in the fluid having a different electrophoretic mobility.

28. A process according to claim 27 and further defined by said rotating being at an angular speed sufficient to induce a plurality of annular vortices at spaced locations along said longitudinal axis.

29. A process according to claim 27 and further defined by said rotating being at an angular speed in excess of 10 revolutions per minute.

30. A process according to claim 27 and further defined by:
maintaining outer surfaces of the approximately annular processing chamber stationary; and
said rotating being accomplished by rotating a rotor defining inner surfaces of the approximately annular processing chamber.

31. A process according to claim 27 and further defined by providing an annular processing chamber not obstructed with transverse dividers along the longitudinal axis thereof.

32. A process for electrophoretically processing, comprising:
feeding an approximately annular processing chamber with a fluid containing at least two chemicals which have differing electrophoretic mobilities; said annular processing chamber having a longitudinal axis and a first end and a second end spaced along said longitudinal axis;
establishing an electrical field having a voltage gradient varying along said longitudinal axis of the processing chamber;
rotating a rotor having surfaces which partially define the annular processing chamber to thereby induce rotational flow in said fluid within the processing chamber;
flowing a counterflow liquid through the processing chamber in a longitudinal direction generally in opposition to migration of at least one of said chemicals;
varying the velocity of the counterflow liquid along the longitudinal axis of the processing chamber to provide varying counterflow conditions used to separate said chemicals due to the varying electrophoretic mobilities thereof;
removing at least two streams from the processing chamber at different longitudinal positions to selectively remove one or more chemicals at each longitudinal position.

33. A process according to claim 32 and further defined by said rotating being at an angular speed sufficient to induce a plurality of annular vortices at spaced locations along with longitudinal axis.

34. A process according to claim 32 and further defined by said rotating being at an angular speed in excess of 10 revolutions per minute.

35. A process according to claim 32 and further defined by:
maintaining outer surfaces of the approximately annular processing chamber stationary; and
said rotating being accomplished by rotating a rotor defining inner surfaces of the approximately annular processing chamber.

36. A process according to claim 32 and further defined by providing an annular processing chamber not obstructed with transverse dividers along the longitudinal axis thereof.

37. A process according to claim 32 and further defined by feeding along a medial position.

38. A process according to claim 32 and further defined by said feeding being continuously feeding, and said removing being continuously removing.

39. A process according to claim 32 and further defined by said feeding being performed by feeding through an infeed inlet port positioned at an infeed location, and removing fluid from an infeed recycle port positioned at a longitudinal position approximating the infeed location.

40. A process according to claim 39 and further defined by recycling fluid removed from the infeed recycle port back to the infeed inlet port.

41. A process according to claim 39 and further defined by:
recycling fluid removed from the infeed recycle port back to the infeed inlet port;
eliminating fluid removed from the infeed recycle port.

42. A process according to claim 39 and further defined by:
recycling fluid removed from the infeed recycle port back to the infeed inlet port;
eliminating fluid removed from the infeed recycle port; said eliminating being accomplished by passing fluid removed from the infeed recycle port adjacent to a filter which reserves desired chemicals in a recycle flow, and forcing fluid through the filter to reduce fluid flow into the processing chamber.

43. An electrophoretic processor comprising:
a stator;
a rotor mounted for rotation about an axis of rotation;
a rotor drive for rotating said rotor;
a processing chamber at least partially defined between the stator and rotor;
a first electrode positioned adjacent a first end of the processing chamber;
a second electrode positioned adjacent a second end of the processing chamber;
multiple fluid access ports at spaced longitudinal positions along said processing chamber to allow fluid communication to or from said processing chamber at multiple locations.

44. An electrophoretic processor according to claim 43 wherein:
said processing chamber is substantially annular about a longitudinal axis;
said multiple fluid access ports extending from said processing chamber in directions substantially perpendicular to the longitudinal axis.

45. An electrophoretic processor according to claim 43 wherein rotor size is adjustable to provide various sized spacings between the stator and the rotor.

46. An electrophoretic processor comprising:
a stator;
an adjustable rotor assembly mounted for rotation about an axis of rotation;
a rotor drive for rotating said rotor;
a processing chamber at least partially defined between the stator and said rotor assembly;
a first electrode positioned adjacent a first end of the processing chamber;
a second electrode positioned adjacent a second end of the processing chamber;
at least one fluid access port allowing fluid communication to or from said processing chamber;
said rotor assembly being adjustable to allow multiple rotor sizes to provide various sized spacings between the stator and the rotor.

47. An electrophoretic processor according to claim 46 wherein the adjustable rotor assembly includes multiple interchangeable rotors of different cross-sectional diameters.

48. An electrophoretic processor according to claim 46 wherein the rotor assembly includes rotor end pieces having differently sized portions for engagement with differently sized rotors.

49. An electrophoretic processor comprising:

a stator;

a rotor mounted for rotation about an axis of rotation;

an indirectly coupled rotor drive for rotating said rotor;

a processing chamber at least partially defined between the stator and rotor;

a first electrode positioned adjacent a first end of the processing chamber;

a second electrode positioned adjacent a second end of the processing chamber;

at least one fluid access port allowing fluid communication to or from said processing chamber.

50. An electrophoretic processor according to claim 49 wherein the rotor drive provides a rotating field.

51. An electrophoretic processor according to claim 49 wherein the rotor drive provides a rotating magnetic field.

* * * * *